United States Patent [19]

Haas et al.

[11] Patent Number: 5,334,778
[45] Date of Patent: Aug. 2, 1994

[54] PROCESS FOR THE PRODUCTION OF 1,3-PROPANEDIOL

[75] Inventors: Thomas Haas, Frankfurt; Norbert Wiegand, Rheinfelden; Dietrich Arntz, Oberursel, all of Fed. Rep. of Germany

[73] Assignee: Degussa Aktiengesellschaft, Frankfurt, Fed. Rep. of Germany

[21] Appl. No.: 63,317

[22] Filed: May 19, 1993

[30] Foreign Application Priority Data

Jun. 3, 1992 [DE] Fed. Rep. of Germany ....... 4218282

[51] Int. Cl.$^5$ ................ C07C 29/141; C07C 31/20
[52] U.S. Cl. ................................................ 568/862
[58] Field of Search ........................................ 568/862

[56] References Cited

U.S. PATENT DOCUMENTS

| | | | |
|---|---|---|---|
| 2,419,300 | 4/1947 | Tollefson | 568/862 |
| 2,421,451 | 6/1947 | Balcar | 568/862 |
| 2,434,110 | 1/1948 | Hatch et al. | 260/602 |
| 2,734,921 | 2/1956 | Bewley et al. | 568/862 |
| 4,094,914 | 6/1978 | Rottig et al. | 568/862 |
| 4,386,018 | 5/1983 | Merger et al. | 568/862 |
| 4,393,251 | 7/1983 | Broecker et al. | 568/862 |
| 4,933,473 | 6/1990 | Ninomiya et al. | 568/862 |
| 5,015,789 | 5/1991 | Arntz | 568/862 |
| 5,171,898 | 12/1992 | Arntz et al. | 568/862 |

FOREIGN PATENT DOCUMENTS

| | | |
|---|---|---|
| 703211 | 2/1965 | Canada ................ 568/862 |
| 2079655 | 4/1993 | Canada . |
| 0412337 | 7/1990 | European Pat. Off. . |
| 0535565 | 9/1992 | European Pat. Off. . |
| 4038192 | 11/1990 | Fed. Rep. of Germany . |
| 3926136 | 4/1991 | Fed. Rep. of Germany . |
| 4132663 | 10/1991 | Fed. Rep. of Germany . |
| 4138981 | 11/1991 | Fed. Rep. of Germany . |
| 4138982 | 11/1991 | Fed. Rep. of Germany . |
| 1335323 | 7/1963 | France . |

*Primary Examiner*—Joseph E. Evans
*Attorney, Agent, or Firm*—Beveridge, DeGrandi, Weilacher & Young

[57] ABSTRACT

1,3-Propanediol produced in a known manner by catalytic hydrogenation of 3-hydroxypropionaldehyde (HPA) obtainable from acrolein has a high residual carbonyl content and leads to problems in the production of poly(1,3-propylene glycol terephthalate). Disclosed is a process for producing 1,3-propanediol having a residual carbonyl content, expressed as propionaldehyde, below 500 ppm and generally below 100 ppm produced in the presence of a fixed-bed or suspension hydrogenation catalyst under an $H_2$ pressure of 5 to 300 bar providing the hydrogenation is carried out at 30° to 80° C. to an HPA conversion of 50 to 95% and is then continued at 100° to 180° C. to an HPA conversion of substantially 100%.

15 Claims, No Drawings

PROCESS FOR THE PRODUCTION OF 1,3-PROPANEDIOL

BACKGROUND AND INTRODUCTION

The present invention relates to a process for the production of 1,3-propanediol having a residual carbonyl content below 500 ppm, expressed as propionaldehyde, by catalytic hydrogenation of 3-hydroxypropionaldehyde in aqueous solution.

1,3-Propanediol has many potential applications as a monomer unit for polyesters and polyurethanes and as a starting material for the synthesis of cyclic compounds.

1,3-Propanediol can be produced by various processes in which the molecule is built up from a $C_2$ and $C_1$ structural element or which preferably start out directly from a $C_3$ structural element, such as in particular acrolein. Where acrolein is used, as for example in the process according to DE-OS 39 26 136 (U.S. Pat. No. 5,015,789, incorporated by reference) or German patent applications P 40 38 192.7 (U.S. Pat. No. 5,171,898, incorporated by reference), P 41 39 981.6 and P 41 38 982.4 (U.S. patent application Ser. No. 07/981,324 filed on Nov. 24, 1992, now U.S. Pat. No. 5,276,201, incorporated by reference), it is hydrated in aqueous phase in the presence of an acidic hydration catalyst to form 3-hydroxypropionaldehyde (HPA).

The aqueous reaction mixture formed in the hydration of acrolein, which contains unreacted acrolein and secondary hydration products, such as 4-oxaheptanedial, and optionally dissolved hydration catalysts in addition to water and 3-hydroxypropionaldehyde, is hydrogenated in the presence of hydrogenation catalysts after removal of the unreacted acrolein and, optionally, part of the water. 1,3-Propanediol is recovered from the reaction mixture thus obtained by distillation and/or extraction based methods known to those skilled in the art.

According to U.S. Pat. No. 2,434,110 (incorporated by reference), catalysts containing one or more hydrogenation-active metals, such as Fe, Co, Ni, Cu, Ag, Mo, W, V, Cr, Rh, Pd, Os, Ir, Ru, or Pt, are suitable for the hydrogenation of 3-hydroxypropionaldehyde to 1,3-propanediol. As described in DE-OS 39 26 136, the catalyst may be present in suspended form per se or fixed to a support or may be a part of fixed-bed catalysts. Homogeneous catalysts may also be used. Such hydrogenation catalysts are well known in the art.

Preferred hydrogenation catalysts which provide for a substantially quantitative conversion of the 3-hydroxypropionaldehyde to 1,3-propanediol are (a) Raney nickel which may be doped with other catalytically active metals, (b) platinum-coated supported catalysts based on metal oxides or active carbon, such as in particular supported catalysts based on titanium dioxide containing 0.1 to 5.0% by weight, based on the support, of Pt in fine-particle form according to German patent application P 41 32 663.6, or (c) nickel-coated oxide- or silicate-containing supported catalysts, such as in particular those based on $Ni/Al_2O_3/SiO_2$. A high volume/time yield is obtained in the hydrogenation reaction when the aqueous reaction mixture to be hydrogenated has an HPA content of 2 to 80% by weight, preferably 5 to 30% by weight and, more preferably, 5 to 20% by weight, and a pH value of 2.5 to 6.5; the hydrogenation temperature is in the range from 30° to 180° C. and the hydrogenation reaction is carried out under hydrogen pressures of 5 to 300 bar.

In the production of 1,3-propanediol on an industrial scale by hydrogenation of 3-hydroxypropionaldehyde in aqueous phase, it has been found that, even under the optimal reaction conditions mentioned above with an HPA conversion of substantially 100% and a selectivity approaching 100%, and despite careful working up of the reaction mixture by distillation and purification of the 1,3-propanediol by distillation, the 1,3-propanediol still has a residual carbonyl content, expressed as propionaldehyde, of a few thousand ppm. This high carbonyl content is extremely troublesome in the production of poly(1,3-propylene glycol terephthalate) and in the application of this polymer for the production of fibers by melt spinning because it leads both to odor emissions and to discoloration of the fibers.

SUMMARY OF THE INVENTION

An object of the present invention was to provide a process for the production of 1,3-propanediol having a reduced residual carbonyl content, preferably below 500 ppm, expressed as propionaldehyde, which would be based on the catalytic hydrogenation of 3-hydroxypropionaldehyde in aqueous phase, more particularly an HPA-containing aqueous reaction mixture from the hydration of acrolein which has been freed from unreacted acrolein.

Accordingly, the present invention relates to a process for the production of 1,3-propanediol having a residual carbonyl content below 500 ppm, expressed as propionaldehyde, by catalytic hydrogenation of 3-hydroxypropionaldehyde (HPA) in aqueous solution in the presence of a fixed-bed or suspension hydrogenation catalyst under a hydrogen pressure of 5 to 300 bar, at a pH value of 2.5 to 6.5, at a temperature of 30° to 180° C., and working up of the reaction mixture by known distillation-based and/or extraction-based measures, characterized in that the hydrogenation is carried out at 30° to 80° C. to an HPA conversion of 50 to 95% and is then continued at 100° to 180° C. to an HPA conversion of substantially 100%.

DETAILED DESCRIPTION OF THE INVENTION

In the hydrogenation of 3-hydroxypropionaldehyde to 1,3-propanediol, the desired reaction is linearly dependent on the reaction time or the space velocity (LHSV=liquid hourly space velocity) and not on the hydrogenation temperature in the case of continuous processes using a fixed-bed catalyst. By contrast, the formation of unwanted secondary products increases exponentially when the temperature is increased. Since the residual carbonyl content in pure 1,3-propanediol was already unsatisfactorily high in the case of hydrogenation at a consistently low temperature, for example 40° to 60° C., it was surprising to find that the residual carbonyl content could be significantly reduced by the hydrogenation process according to the present invention with at least a first temperature stage in the range from 30° to 80° C., and preferably 40° to 70° C., and at least a second temperature stage in the range from 100° to 180° C. and preferably 110° to 150° C.

The residual carbonyl content in the pure 1,3-propanediol produced in accordance with the present invention is generally far below 500 ppm (10 ppm to less than 500 ppm), mostly below 150 ppm (10 ppm to less than 150 ppm), and preferably below 100 ppm (10 ppm to less than 100 ppm), expressed as propionaldehyde. The goal of the present invention is to reduce the residual carbonyl content to approximately 0 ppm. The carbonyl content may be determined either in a known manner gravimetrically or, in the case of relatively low contents, preferably by HPLC and UV detection after conversion of the carbonyl compounds into the dinitrophenyl hydrazones in a manner known in the art. The residual carbonyl content thus determined also includes aldehydes present in acetalized form, such as for example acetals from 3-hydroxypropionaldehyde and 1,3-propanediol.

The hydrogenation is carried out by methods known in the art in known reactors, the liquid reaction mixture, the catalyst and hydrogen being thoroughly contacted with one another. In the case of suspension hydrogenation, stirred reactors or flow reactors are particularly suitable, the temperature stages according to the present invention being established one behind the other at a time interval determined in preliminary tests or being arranged spatially one behind the other in a reactor system. The suspension hydrogenation is carried out at a temperature of preferably 40° to 60° C. to an HPA conversion of 50 to 80% and is then continued, preferably at 110° to 150° C., to an HPA conversion of substantially 100%.

The embodiment of the present invention in a fixed-bed hydrogenation reactor equipped with a fixed-bed catalyst is particularly suitable for the hydrogenation of 3-hydroxypropionaldehyde on an industrial scale and preferably for the hydrogenation of an HPA-containing aqueous reaction mixture from the hydration of acrolein which has been freed from unreacted acrolein. In a reactor such as this, the liquid reaction mixture flows or trickles over the fixed-bed catalyst together with the hydrogen introduced. Fixed beds are understood to be both beds of the shaped catalyst (for example extrudates, pellets, or beads) and also hydrogenation catalysts fixed to large-surface shaped supports (for example ceramic honeycombs). To ensure good distribution of the hydrogen in the reaction mixture and uniform distribution of the gas/liquid mixture over the entire cross-section of the fixed bed, the liquid reaction mixture and the hydrogen may be passed together through static mixers before the catalyst bed. The reactor is equipped in such a way that a reaction temperature of 30° to 80° C. (and preferably 40° to 70° C.) is established and can be maintained in a first zone of the catalyst bed which makes up about 50 to 95% (preferably 75 to 90% and more preferably 80 to 90% of the volume), and a reaction temperature of 100° to 180° C. (and preferably 110° to 150° C.) is established and can be maintained in a second zone with the remaining volume of the catalyst bed. The temperature zones mentioned may have a substantially constant temperature or an increasing temperature profile within the particular range. There is of course a heating zone between the first and second temperature zones.

The space velocity in the catalyst bed is adjusted in such a way that a substantially quantitative HPA conversion is obtained for a constant temperature throughout the catalyst bed, for example 60° C. By dividing up the catalyst bed into the temperature zones according to the present invention, the residual carbonyl content in the pure 1,3-propanediol can be reduced to values below 500 ppm and mostly below 100 ppm for the same space velocity.

Hydrogenation catalysts which have been used with particular success in the prior art and which were described in the introduction to this specification are particularly suitable for the process according to the present invention. Particularly suitable catalysts for the suspension hydrogenation are Raney nickel catalysts and supported catalysts based on Pt or Ru on active carbon, $Al_2O_3$, $SiO_2$ or $TiO_2$. The supported catalysts mentioned above, and nickel on oxide- or silicate-containing supports, are particularly suitable for the fixed-bed hydrogenation. The hydrogenation conditions in regard to HPA concentration, H2 pressure and pH value also correspond to the prior art.

The 1,3-propanediol produced in accordance with the present invention with its low residual carbonyl content of generally below 100 ppm, expressed as propionaldehyde, is particularly suitable for the production of polypropylene glycol terephthalate fibers with no odor emissions or discoloration during the polycondensation and spinning steps. In addition to achieving this quality advantage of the 1,3-propanediol, the process according to the present invention is also distinguished by the fact that it is easy to carry out. Unexpectedly, the method according to the present invention does not reduce either selectivity or yield.

The process according to the invention is illustrated by the following Examples. The embodiment with a fixed-bed catalyst and, in particular, a $Pt-TiO_2$ supported catalyst (according to German patent application P 41 32 663.6 (corresponding to U.S. patent application Ser. No. 07/948,718 filed on Sep. 24, 1992, incorporated by reference) or an $Ni/Al_2O_3/SiO_2$ catalyst is regarded as the best embodiment.

Examples 1 and 2 and Comparison Examples 1 and 2a to 2c-Hydrogenation of an aqueous solution of 3-hydroxypropanal (HPA) in a trickle-bed reactor.

The aqueous HPA solution was prepared by hydration of acrolein, for which purpose a 16.9% by weight aqueous acrolein solution was passed through an ion exchanger fixed bed (RLewatit TP 208, H Form, a product of Bayer AG) at a constant reaction temperature of 60° C. and at a space velocity (LHSV) of 0.54 $h^{-1}$. The solution was freed from unreacted acrolein under reduced pressure at 65° C.

A trickle-bed reactor having a volume of 1.3 liters was used for the continuous hydrogenation in a trickle bed. The reactor consisted of a liquid reservoir, a preheating zone, the fixed-bed reactor and a liquid separator. Using heat transfer oil circuits, the reactor temperature $T_{R1}$ was established along the first approximately 85% of the reactor bed while the reactor temperature $T_{R2}$ was established along the remaining approximately 15% of the reactor bed. The pressure and flow of hydrogen were electronically controlled. The aqueous HPA solution was pumped into the stream of hydrogen before the preheating zone and the mixture was introduced at the head of the reactor (trickle bed operation). After passing through the reactor, the product formed was removed from the separation vessel at regular intervals and the hydrogen was continuously recycled by a compressor. The product was analyzed for unreacted HPA by HPLC and the 1,3-propanediol formed was determined by GC. Water was first distilled off from the hydrogenated reaction mixture and the crude 1,3-propanediol was then subjected to fractional distillation (boiling point of the pure 1,3-propanediol 134° C./50 mbar).

In Example 1 and Comparison Example 1 (CE1), the reactor bed was filled with a commercially available fixed-bed nickel catalyst in the form of extrudates (diameter 1.6 mm in CE1, 0.8 mm in Example 1) of the $Ni/Al_2O_3/SiO_2$ type with an Ni content of approximately 30%.

In Example 2 and Comparison Examples 2a to 2c (CE 2a to CE 2c), the reactor bed was filled with a supported catalyst in the form of 1.6 mm diameter, 10 mm long extrudates based on pyrogenic titanium dioxide containing 2% by weight platinum deposited thereon in fine-particle form (according to German patent application P 41 32 663.6).

The reaction conditions prevailing during hydrogenation and the results are set out in Table 1 where $P_{H2}$ stands for the hydrogen pressure in bar; LHSV is the space velocity in hours$^{-1}$; $C_{HPA/E}$ and $C_{HPA/P}$ stand for the concentration of HPA (% by weight) in the educt and in the hydrogenated reaction mixture; $C_{PD/P}$ stands for the concentrations (% by weight) of propanediol in the hydrogenated reaction mixture; $T_{R1}$ and $T_{R2}$ are the temperatures (° C.) in reactor zones 1 and 2; U is the conversion in %, S is the selectivity in %; Carb is the residual carbonyl content in the 1,3-propanediol after fractional distillation in ppm (parts per million), expressed as propionaldehyde.

TABLE 1

| Example No. | $P_{H2}$ (bar) | LHSV ($h^{-1}$) | $T_{R1}$ (°C.) | $T_{R2}$ (°C.) | $C_{HPA/E}$ (% by weight) | $C_{HPA/P}$ (% by weight) | $C_{PD/P}$ (%) | U (%) | S (ppm) | Carb |
|---|---|---|---|---|---|---|---|---|---|---|
| 1 CE | 100 | 0.8 | 55 | 55 | 10.8 | 0.11 | 10.7 | 96.5 | 98 | 10,000 |
| 1 | 100 | 1.0 | 50 | 125 | 8.9 | <0.001 | 9.2 | 100 | 100 | <100 |
| 2a CE | 90 | 0.8 | 60 | 60 | 10.1 | 0.03 | 10.4 | 99.7 | 100 | 3,000 |
| 2 | 90 | 0.8 | 60 | 140 | 10.1 | <0.001 | 10.5 | 100 | 100 | <100 |
| 2b CE | 34 | 0.6 | 60 | 60 | 11.1 | 3.03 | 7.6 | 72.8 | 91.6 | n.d. |
| 2c CE | 34 | 0.6 | 70 | 70 | 11.1 | 1.02 | 8.7 | 90.8 | 84.3 | n.d. |

It follows from Comparison Examples 2b and 2c that, although the conversion is increased in the known process by an increase in temperature, selectivity is reduced. In the process according to the present invention, Example 2, selectivity is 100% despite a high temperature in section R2 of the reactor.

Comparison of Example 1CE with Example 1 and Example 2CE with Example 2 shows that it is possible by the process according to the present invention to produce 1,3-propanediol having a residual carbonyl content below 100 ppm, expressed as propionaldehyde, without any loss of yield.

Example 3 and Comparison Examples 3a and 3b-Hydrogenation of an aqueous solution of 3-hydroxypropionaldehyde (HPA) in a suspension hydrogenation reactor. The aqueous HPA solution was prepared in the same way as in Examples 1 and 2 and CE1 and CE2.

500 g of the HPA solution were introduced into a 1000 ml autoclave equipped with an aerating stirrer and hydrogenated under hydrogen pressure at a certain reaction temperature, at a stirrer speed of 1000 r.p.m., and in the presence of 7.5 g Raney nickel. The reaction conditions and the results are set out in Table 2. The abbreviations in the column headings of Table 2 have the same meanings as in Table 1, except that $T_1$ and $T_2$ are the temperatures (° C.) during the first and second hydrogenation phases and $t_1$ and $t_2$ are the associated reaction times (minutes). On completion of hydrogenation, $C_{HPA/P}$ and $C_{PD/P}$ were determined and the conversion and selectivity were determined therefrom with $C_{HPA/E}$. Water was distilled off from the hydrogenated reaction mixture and the remaining crude 1,3-propanediol was subjected to fractional distillation.

TABLE 2

| Example No. | $P_{H2}$ (bar) | $T_1:T_2$ (°C.) | $t_1 + t_2$ (mins.) | $C_{HPA/E}$ (% by weight) | $C_{HPA/P}$ (% by weight) | $C_{PD/P}$ (%) | U (%) | S (ppm) | Carb |
|---|---|---|---|---|---|---|---|---|---|
| CE 3a | 80 | 50:50 | 40 | 11.38 | 0.29 | 11.17 | 97.5 | 98.0 | 16,200 |
| CE 3b | 80 | 50:50 | 180 | 11.38 | 0.19 | 11.43 | 98.3 | 99.5 | 13,000 |
| 3 | 80 | 50:120 | 20 + 20 | 11.38 | 0.0015 | 11.64 | 100 | 99.6 | 110 |

Further variations and modifications of the foregoing will be apparent to those skilled in the art and such variations and modifications are attended to be encompassed by the claims that are appended hereto.

German Priority Application P 42 18 282.4, filed on Jun. 3, 1992, is relied on and incorporated by reference.

What is claimed:

1. A process for the production of 1,3-propanediol having a residual carbonyl content below 500 ppm, expressed as propionaldehyde, comprising catalytically hydrogenating 3-hydroxypropionaldehyde in aqueous solution in the presence of a hydrogenation catalyst at (a) 30° to 80° C. to an 3-hydroxypropionaldehyde conversion of 50 to 95% and (b) then continuing said hydrogenating at 120° to 140° C. to achieve an 3-hydroxypropionaldehyde conversion of substantially 100%.

2. The process according to claim 1, wherein said temperature in (a) is 40° to 70° C.

3. The process according to claim 1, wherein said 3-hydroxypropionaldehyde conversion in (a) is 50 to 80%.

4. The process according to claim 1, wherein said residual carbonyl content is below 150 ppm.

5. The process according to claim 1, wherein said residual carbonyl content is below 100 ppm.

6. The process according to claim 1, wherein said hydrogenation is carried out in a fixed-bed hydrogenation reactor with a temperature profile increasing in stages in the catalyst bed, the reaction temperature in the first part of the catalyst bed, which makes up 50 to 95% of the total catalyst bed, being in the range from 30° to 80° C. and the reaction temperature in the remaining part of the catalyst bed being in the range from 120° to 140° C.

7. The process according to claim 6, where said first part of the catalyst bed makes of 75 to 90% of the total catalyst bed.

8. The process according to claim 6, where said first part of the catalyst bed makes of 80 to 90% of the total catalyst bed.

9. The process according to claim 6, wherein said fixed-bed hydrogenation reactor is a trickle-bed reactor.

10. The process as claimed in claim 1, wherein said hydrogenation is carried out in a suspension hydrogenation reactor at 40° to 60° C. to an 3-hydroxypropionaldehyde conversion of 50 to 80% and is continued at 120° to 140° C. to an 3-hydroxypropionaldehyde conversion of substantially 100%.

11. The process according to claim 10, wherein said suspension hydrogenation reactor is a stirred reactor.

12. The process according to claim 1, wherein said hydrogenation catalyst is (a) Raney nickel optionally doped with other hydrogenation-active metals, (b) supported catalysts based on platinum- or ruthenium-coated active carbon or metal oxides or (c) nickel-coated oxide- or silicate-containing supported catalysts.

13. The process according to claim 12, wherein said oxides in (b) are $Al_2O_3$, $SiO_2$ or $TiO_2$.

14. The process according to claim 12, wherein said catalysts in (c) are based on $Ni/Al_2O_3/SiO_2$.

15. The process according to claim 1, wherein said process is conducted in at least two reaction zones, wherein step (a) is conducted in one reaction zone and step (b) is conducted in a second reaction zone.

* * * * *